(12) United States Patent
Itoi

(10) Patent No.: US 8,088,064 B2
(45) Date of Patent: Jan. 3, 2012

(54) SLIDABLE COVER FOR ENDOSCOPE CONTROL APPARATUS

(75) Inventor: Hiromu Itoi, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1090 days.

(21) Appl. No.: 11/869,034

(22) Filed: Oct. 9, 2007

(65) Prior Publication Data
US 2008/0086030 A1  Apr. 10, 2008

(30) Foreign Application Priority Data
Oct. 10, 2006 (JP) ................ P2006-276909

(51) Int. Cl.
*A61B 1/00* (2006.01)
(52) U.S. Cl. ....................... 600/132; 600/131
(58) Field of Classification Search .......... 600/132, 600/131, 134; 220/200, 241, 242, 250, 252, 220/253, 348, 536, 805, 812
See application file for complete search history.

(56) References Cited

U.S. PATENT DOCUMENTS

| 3,828,393 | A | * | 8/1974 | Pierie .................................. 16/65 |
| 4,601,284 | A | * | 7/1986 | Arakawa et al. .............. 600/112 |
| 5,702,345 | A | * | 12/1997 | Wood et al. ................... 600/109 |
| 5,830,124 | A | * | 11/1998 | Suzuki et al. ................. 600/134 |
| 6,951,469 | B1 | * | 10/2005 | Lin ................. 439/135 |
| 7,866,003 | B2 | * | 1/2011 | Tooyama ........................ 16/422 |
| 2004/0106851 | A1 | * | 6/2004 | Amling et al. ................ 600/110 |
| 2005/0000057 | A1 | * | 1/2005 | Tsekhanovsky et al. ......... 16/79 |
| 2006/0052664 | A1 | * | 3/2006 | Julian et al. .................. 600/146 |
| 2006/0116550 | A1 | * | 6/2006 | Noguchi et al. .............. 600/132 |

FOREIGN PATENT DOCUMENTS
JP 2001-340337 A 12/2001
* cited by examiner

*Primary Examiner* — John P Leubecker
*Assistant Examiner* — Victoria Chen
(74) *Attorney, Agent, or Firm* — Birch, Stewart, Kolasch & Birch, LLP

(57) ABSTRACT

An ultrasonic control apparatus has a connector and a connector cover. The connector cover is attached to be slidable between a close position where the connector is covered and an open position where the connector is exposed, and has a press projection. When the connector is set on the press projection and then pressed down together with the connector cover, the connector is exposed and opposed to the connector, and the connectors can be connected with each other.

8 Claims, 5 Drawing Sheets

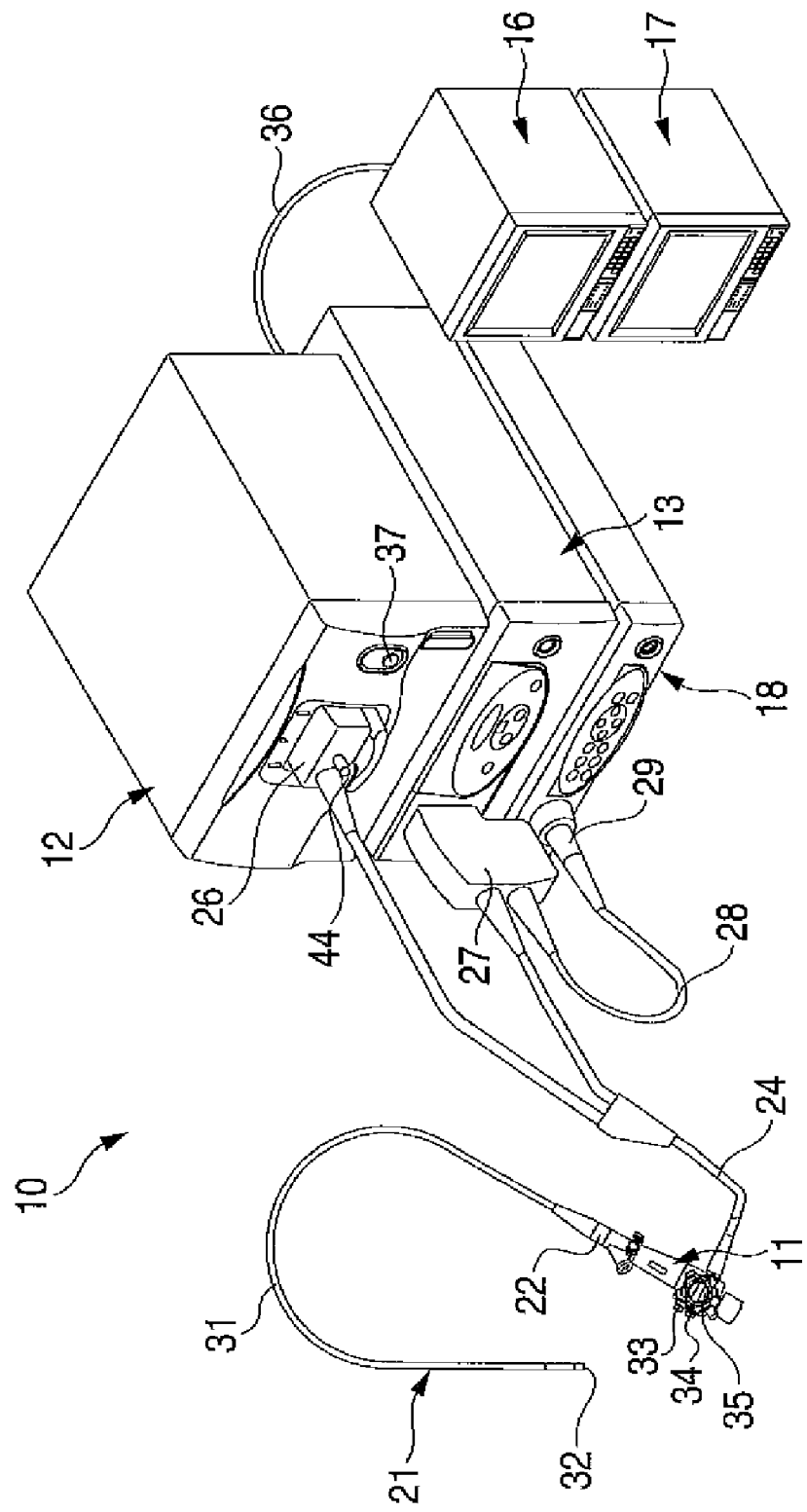

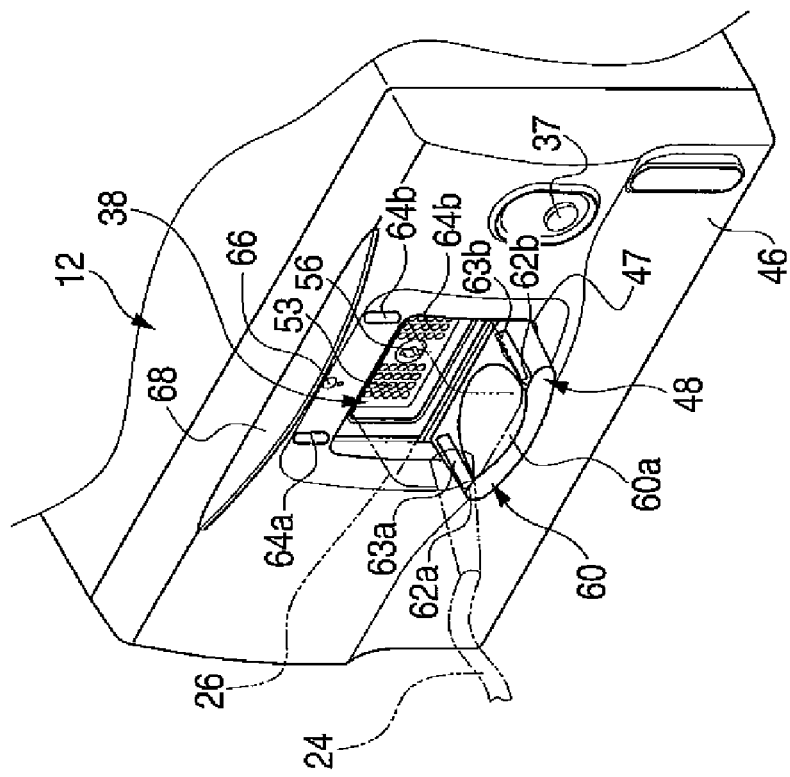
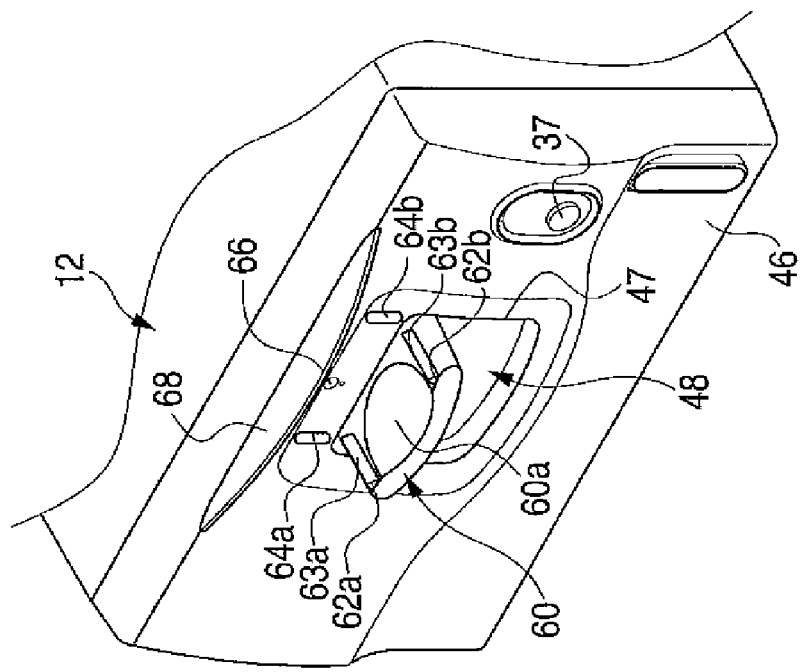

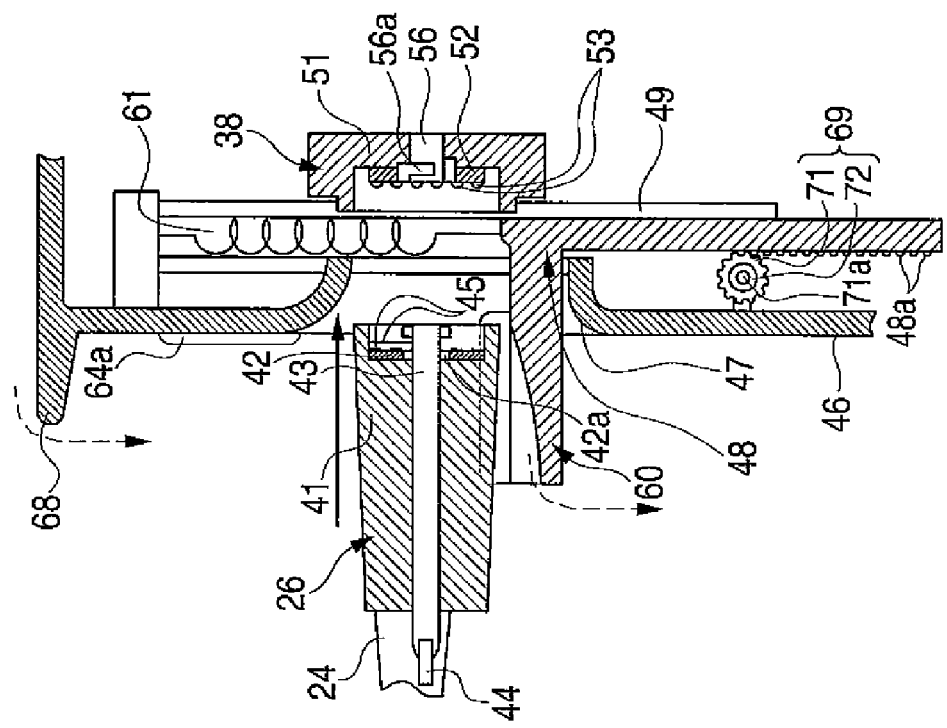
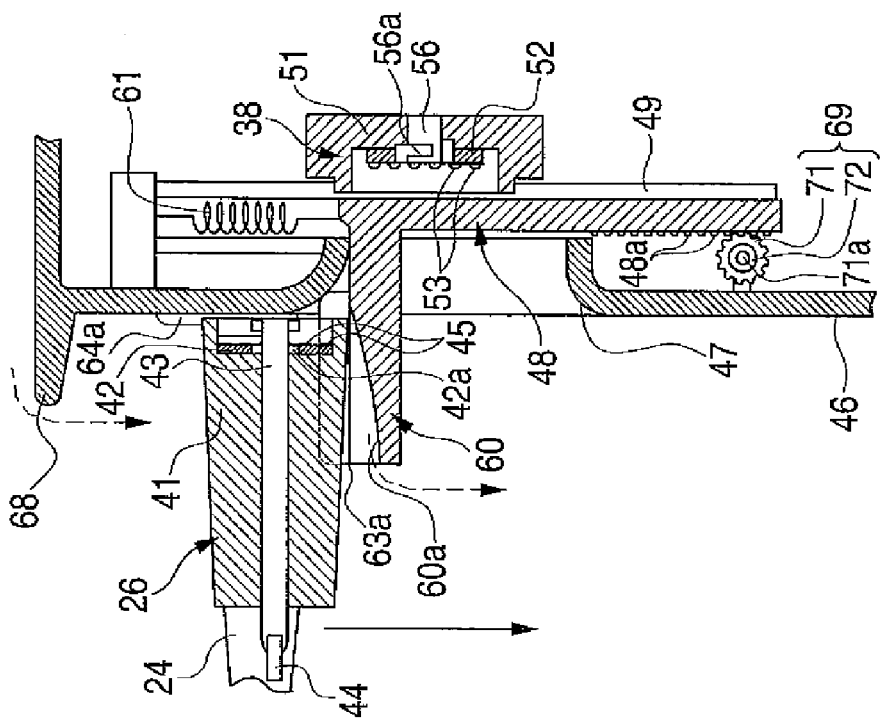
FIG. 3A
FIG. 3B

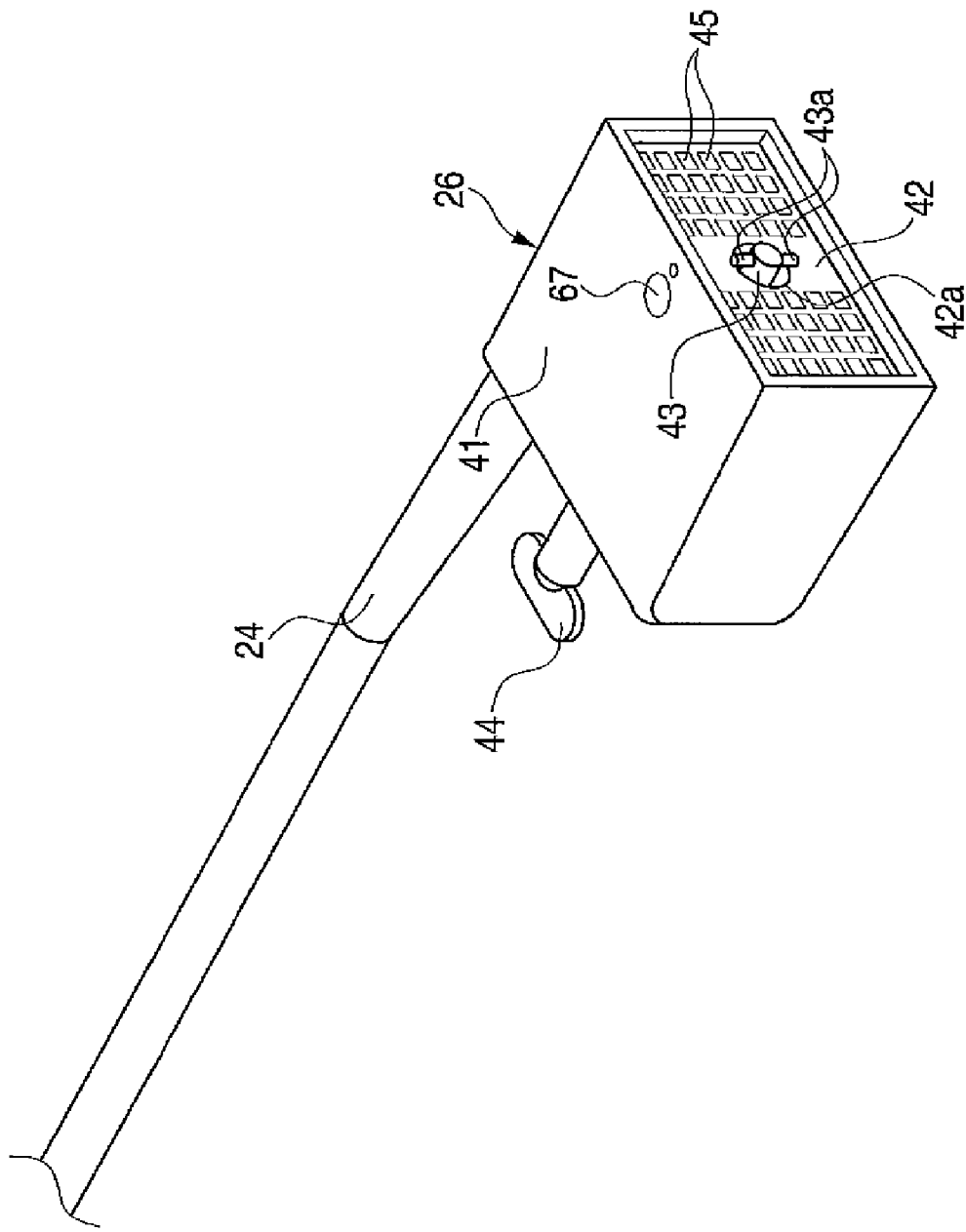

SLIDABLE COVER FOR ENDOSCOPE CONTROL APPARATUS

BACKGROUND OF THE INVENTION

1. Field of the Invention

The present invention relates to an endoscope apparatus for performing a diagnosis in the body.

2. Description of the Related Art

In the related Art, an endoscope apparatus configured by an endoscope which is to be used while being inserted into the body, and a control apparatus which is connected with the endoscope to perform a display on a monitor, data analysis, and the like is known. As disclosed in, for example, JP-A-2001-340337, in such an endoscope apparatus, the endoscope must be detachably connected with the control apparatus via a flexible cord. Therefore, connectors for connection are disposed respectively in the tip end of the flexible cord and the control apparatus, and the connectors are coupled to each other to set the endoscope and the control apparatus to a connection state.

In an endoscope, particularly in an ultrasonic endoscope, it is often that liquids such as degassed water serving as an ultrasonic transmission medium, body fluid, and washing water adhere to the endoscope. A control apparatus comprises many electronic components, an electric power source, and the like. When a liquid, dust, or the like enters the control apparatus through the vicinity of the connectors, a failure or a malfunction occurs. In an endoscope apparatus, therefore, a cap or a slide cover is disposed in order to protect such connectors.

In the related-art endoscope apparatus, however, much trouble is experienced in an operation in which a cap is removed or a cover is opened or closed before connectors are connected with or disconnected from each other. Therefore, the connecting operation cannot be smoothly performed. In the case of an endoscope apparatus having a protective cap, particularly, it is cumbersome to remove the cap, and there is a possibility that, when a wet hand is contacted with the cap, a liquid adheres to the connectors, or that the cap itself is lost. In a control apparatus having a slide cover, usually, the cover must be pushed from the lower side to the upper side so as to expose an internal connector. In the case where the user holds the endoscope with both hands, it is difficult to perform an operation of opening or closing the cover, and hence the ease of use is very poor. As means for moving the cover at the open position to the close position, free fall due to gravity, or manual movement must be employed. Therefore, the cover cannot be surely returned to the close position.

SUMMARY OF THE INVENTION

The invention has been conducted in view of the above-discussed problems. It is an object of the invention to provide an endoscope apparatus in which connectors for an endoscope and a control apparatus can be connected with each other surely and easily while maintaining excellent waterproof and dustproof properties of the connectors.

In order to attain the object, according to the invention, there is provided an endoscope apparatus comprising: an endoscope comprising an endoscope connector in one end portion; and a control apparatus that controls the endoscope, the control apparatus comprising: a case having an opening; a control-apparatus connector in an inner part of the opening, the control-apparatus connector being to be connected with the endoscope connector; a connector cover attached to be slidable between a close position where the control-apparatus connector is covered and an open position where the control-apparatus connector is exposed, the open position being located below the close position, wherein the connector cover comprises a press projection that is formed integrally with the connector cover, that is substantially perpendicular to a slide direction, projecting toward an outside of the case, and that is formed in accordance with the endoscope connector; and an urging member that urges the connector cover from the open position to the close position, wherein, when the endoscope connector is placed on the press projection and pressed down, the connector cover is moved from the close position to the open position against an urging force of the urging member, so as to enable the endoscope connector to be connected with the control-apparatus connector through the opening. Preferably, the press projection integrally comprises, in its both end portions, inducing taper portions that guide the endoscope connector toward a connecting position where the endoscope connector is to be connected with the control-apparatus connector. Preferably, the case integrally comprises, above the opening, a guide piece that guides the endoscope connector toward the press projection.

Preferably, each of the case and the endoscope connector comprises a positioning mark, and the endoscope connector is aligned to a predetermined direction with respect to the control-apparatus connector by matching positions of the positioning marks with each other. Preferably, the control apparatus further comprises a damper member that resists the urging force of the urging member to reduce a speed of the connector cover that returns from the open position to the close position.

BRIEF DESCRIPTION OF THE DRAWINGS

FIG. 1 is a diagram showing the configuration of the endoscope apparatus of the invention;

FIGS. 2A and 2B are diagrams showing the configuration of the periphery of a connector of a control apparatus;

FIGS. 3A and 3B are section views of main portions showing a process of connecting connectors with each other;

FIG. 4 is a perspective view showing an endoscope connector; and

DETAILED DESCRIPTION OF THE INVENTION

Figure 5:
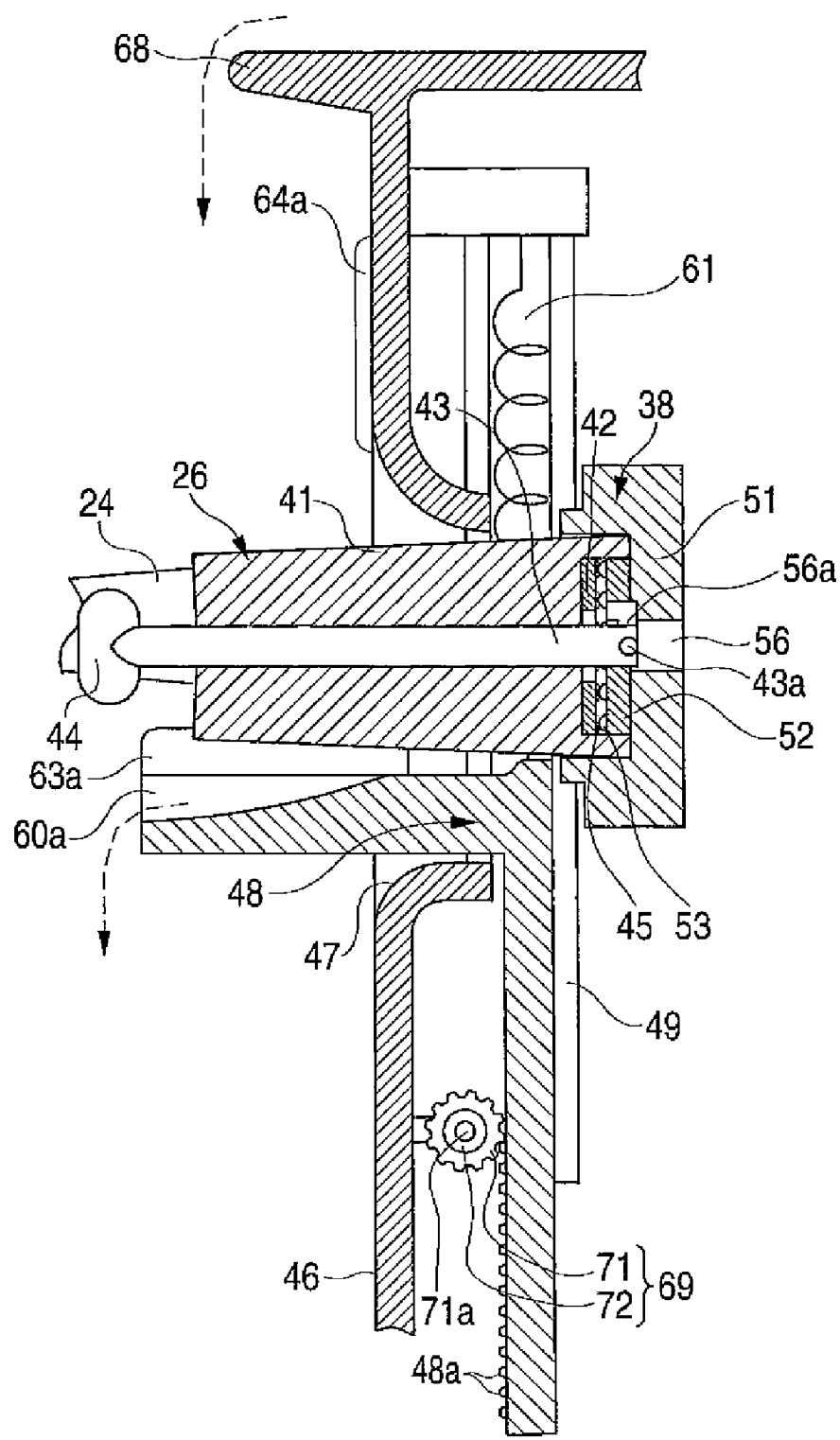
FIG. 5 is a section view of main portions showing a connection state.

Hereinafter, en embodiment of the invention will be described in detail with reference to the accompanying drawings. FIG. 1 shows the whole configuration of an endoscope apparatus. The endoscope apparatus 10 is configured by: an ultrasonic endoscope 11; an ultrasonic control apparatus (control apparatus) 12 which produces an ultrasonic image due to the ultrasonic endoscope 11; a light source apparatus 13; display devices 16, 17; and a processor 18 which produces an optical image (electronic image) due to the ultrasonic endoscope 11.

The ultrasonic endoscope 11 is configured by an insertion part 21 which is to be inserted into a body cavity, and an operation part 22 which is coupled to a basal end portion of the insertion part 21. One end portion of a universal cord 24 is coupled to a side portion of the operation part 22. The universal cord 24 branches off in the middle. The other end portions are coupled to an endoscope connector 26 and a light source control connector 27, respectively. One end portion of a processor cable 28 is coupled to a side portion of the light source control connector 27. A processor connector 29 is coupled to the other end portion of the processor cable.

The insertion part 21 is configured by a flexible cord 31 which is small in diameter and long, and which is flexible, and a tip end portion 32 which is disposed in a tip end of the flexible cord 31. A basal end portion of the flexible cord 31 is coupled to a tip end portion of the operation part 22.

An ultrasonic transducer is incorporated in the tip end portion 32. When the ultrasonic transducer is driven, ultrasonic pulses are transmitted into the body, and a reflection echo is obtained from the body tissues. The reflection echo is received by the ultrasonic transducer to be converted into an electric signal (ultrasonic signal). Then, the signal is output.

In the operation part 22, an air/water supply button 33 for performing air and water supplying operations, a suction button 34 for performing a sucking operation, and an angle knob 35 for controlling the bending of the tip end portion 32 to a desired direction. Although not illustrated in detail, the tip end portion 32 comprises an imaging optical system, and an image pickup device such as a CCD, so that an image of the interior of the body is taken, electronic image data are formed, and the data are output through the universal cord 24.

A connector (not shown) is disposed in the light source apparatus 13. The light source control connector 27 of the ultrasonic endoscope 11 is detachably coupled to the connector. When the ultrasonic endoscope 11 is in a connection state, the light source apparatus 13 supplies illumination light for illuminating an observation area to an illumination system of the ultrasonic endoscope 11.

Although not illustrated in detail, the ultrasonic control apparatus 12 incorporates: a power source unit; a transmission/reception circuit unit which produces a driving signal for generating an ultrasonic wave, and which applies a signal process to a received ultrasonic signal; a signal processing circuit which applies a signal process to received data in the form of an analog signal output from the transmission/reception circuit unit, to form an ultrasonic diagnosis image; and the like. The display device 16 is connected with the ultrasonic control apparatus 12 via a communication cable 36 to display an ultrasonic diagnosis image based on an ultrasonic signal output from the insertion part 21. The display device 17 is connected with the processor 18 to display an electronic image taken by the ultrasonic endoscope 11. A main switch 37 and the like are disposed in the ultrasonic control apparatus 12.

As shown in detail in FIGS. 2A, 2B, 3A and 3B, a control-apparatus connector 38 is further disposed in the ultrasonic control apparatus 12. The endoscope connector 26 is detachably connected with the control-apparatus connector 38. Hereinafter, the configuration of the periphery of the control-apparatus connector 38 and the endoscope connector 26 will be described. As shown in FIG. 4, the endoscope connector 26 is configured by: a connector body 41 which is continuous to the universal cord 24; a contact board 42 which is incorporated in an end face of the connector body 41; a lock member 43 which protrudes from an opening 42a formed in the contact board 42; and a nip member 44. Many contacts 45 are mounted on the contact board 42. The upper and lower faces of the connector body 41 are formed as inclined faces which are inclined with respect to a horizontal plane when the control-apparatus connector 38 and the endoscope connector 26 are in the connection state (see FIG. 5). Even when a liquid or the like adheres to the connector body 41, the liquid slides down the inclined face of the connector body and drops off to the outside, and therefore a liquid does not enter the interior of a case 46.

Engaged projections 43a which project from the cylindrical outer peripheral face are formed integrally on the lock member 43. The engaged projections 43a are engaged with an engagement groove 56a of the control-apparatus connector 38 which will be described later. The lock member 43 is passed through the interior of the connector body 41 to project into the opposite side. The nip member 44 is formed integrally with a tip end portion of the member. When the user rotates the nip member 44 while nipping the member, the lock member 43 is integrally rotated.

As shown in FIGS. 2A, 2B, 3A and 3B, the control-apparatus connector 38 is disposed in an inner part of an opening 47 formed in the case 46 of the ultrasonic control apparatus 12. Furthermore, a connector cover 48 is disposed in the ultrasonic control apparatus 12. The connector cover 48 is supported by a slide rail 49 disposed inside the case 46, and attached to the case 46 so as to be slidable between a close position which is located on the back side of the opening 47, and in which the control-apparatus connector 38 is covered (the state shown in FIGS. 2A and 3A), and an open position which is located below the close position, and in which the control-apparatus connector 38 is exposed (the state shown in FIGS. 2B and 3B). As shown in detail in FIG. 5, the control-apparatus connector 38 is configured by a connector case 51, and a contact board 52. The connector case 51 is formed into a box-like shape corresponding to the outer shape of the endoscope connector 26. The contact board 52 is fitted to the inner side of the connector case. Contacts 53 in which the number and the arrangement are matched with those of the contacts 45 of the endoscope connector 26 are mounted on the contact board 52. A through hole 56 is formed in the middles of the contact board 52 and the connector case 51. The through hole 56 is opened so as to match with the lock member 43 of the endoscope connector 26, and the engagement groove 56a (see FIGS. 2A and 2B) which, when the lock member 43 is inserted to the inner part, butts against the engaged projections 43a is formed. When the lock member 43 is inserted into the through hole 56, the lock member 43 is rotated by 90° in a predetermined direction while nipping the nip member 44, and then the engaged projections 43a is engaged with the engagement groove 56a. As a result, a locked state where the endoscope connector 26 is prevented from being disconnected from the control-apparatus connector 38 is attained (the state shown in FIG. 5). When the locked state is to be canceled, the lock member 43 is rotated by 90° in the reverse direction, and the engagement of the engaged projections 43a by the engagement groove 56a is canceled, with the result that disconnection of the endoscope connector 26 is enabled.

In the connector cover 48, a press projection 60 is integrally formed. The press projection projects toward the outside of the case 46 with passing through the opening 47, along a horizontal direction which is substantially perpendicular to the slide direction. The press projection 60 is formed to be about one size larger than the endoscope connector 26 and correspond thereto. An urging member 61 which urges the connector cover 48 from the open position to the close position is disposed inside the case 46. In the embodiment, a coil spring is used as the urging member 61. The urging member is not restricted to this. Any member such as a plate spring may be used as far as it can urge the connector cover 48. When the endoscope connector 26 is placed on the press projection 60 and pressed down, the connector cover 48 is moved from the close position to the open position against the urging force of the urging member 61, thereby enabling the endoscope connector 26 to be connected with the control-apparatus connector 38 through the opening 47.

In the press projection 60, guide projections 62a, 62b are disposed integrally with both end portions, respectively. The guide projections 62a, 62b have taper portions 63a, 63b which are gradually inclined toward the center of the press projection 60, respectively. When the endoscope connector 26 is placed on the upper face of the press projection 60, the connector is induced to the center position of the press projection 60 by guidance of the taper portions 63a, 63b, and set to a connecting position opposed to the control-apparatus connector 38. Then, the endoscope connector 26 which is opposed to the control-apparatus connector 38 is inserted along the press projection 60, whereby the connecting operation can be performed.

In the press projection 60, a slope 60a which are gradually lowered from the control-apparatus connector 38 toward the tip end is formed in the vicinity of the middle. Even when a liquid adheres to the press projection 60, the liquid slides down the slope 60a and drops off to the outside, and therefore the liquid enters the interior of the case 46.

In the case 46, guide pieces 64a, 64b which guide the endoscope connector 26 toward the press projection 60 are integrally disposed above the opening 47. The guide pieces 64a, 64b are formed at an interval corresponding to the endoscope connector 26 so as to extend in the vertical direction.

The case 46 and the endoscope connector 26 comprise positioning marks 66, 67, respectively. The mark 66 is positioned at approximately the midpoint between the guide pieces 64a, 64b, and the mark 67 is formed on a predetermined face of the endoscope connector 26 and at a position in the vicinity of the end. When the positions of the marks 66, 67 having the same pattern are made coincident with each other, the endoscope connector 26 can be aligned to a predetermined direction with respect to the control-apparatus connector 38.

In the case 46, a peak portion 68 for receiving a liquid is disposed above the opening 47 and the guide pieces 64a, 64b. Even when a liquid drops from the ultrasonic endoscope 11 or the hand of the user, the peak portion 68 receives the liquid, and the liquid can be prevented from entering the interior of the case 46. Furthermore, a liquid dropping from the peak portion 68 is received by the slope 60a of the connector cover 48, and therefore the liquid does not enter the interior of the case 46.

A damper member 69 is placed at a position which is sandwiched between the inner wall face of the case 46 and the connector cover 48. The damper member 69 is configured by a friction member 71 supported by a center shaft 71a, and a gear member 72 which slides over the outer peripheral face of the friction member 71. The gear member 72 meshes with a rack gear 48a formed on the connector cover 48 to be rotated in conjunction with slide movement of the connector cover 48. When the gear member 72 is rotated, a frictional resistance is produced between the gear member and the friction member 71. The frictional resistance is produced when the connector cover 48 slides, and hence the damper member 69 resists the urging force of the urging member 61 to reduce the speed of the connector cover 48 in the case where the connector cover returns from the open position to the close position. When the connector cover 48 returns to the close position, the connector cover slidingly moves at a low speed. Therefore, the periphery of the connector cover 48 can be prevented from being damaged and breaking down, and a foreign material can be prevented from entering between the damper member and the connector cover 48.

The function of the configuration will be described. When the ultrasonic endoscope 11 is to be connected with the ultrasonic control apparatus 12, the user first causes the endoscope connector 26 to butt against the guide pieces 64a, 64b of the case 46, and matches the positions of the positioning marks 66, 67 with each other. Then, the endoscope connector 26 is downward moved along the guide pieces 64a, 64b, and guided to the upper face of the press projection 60. At this time, the endoscope connector 26 is set to the center position of the press projection 60, by guidance of the taper portions 63a, 63b.

When the user presses down the endoscope connector 26 which is set on the press projection 60, the connector cover 48 is moved from the close position to the open position as described above, and the endoscope connector 26 is opposed to the control-apparatus connector 38. Then, the endoscope connector 26 is caused to enter into the opening 47 along the press projection 60, and the endoscope connector 26 is inserted into the control-apparatus connector 38 to cause the contacts 45, 53 to be contacted with each other, thereby attaining the connection state. In this state, when the nip member 44 is rotated by 90° in a predetermined direction, the locked state is attained, so that the endoscope connector 26 is not disconnected (the state shown in FIG. 5).

In this way, the connection between the endoscope connector 26 and the control-apparatus connector 38 can be performed easily and surely by a simple operation. Moreover, when the endoscope connector 26 is disconnected from the control-apparatus connector 38 after an ultrasonic image due to the insertion part 21 is obtained, the connector cover 48 is caused to return to the close position by the urging force of the urging member 61. Therefore, the case 46 can hold excellent waterproof and dustproof properties.

In the above, the endoscope apparatus comprising the ultrasonic endoscope in which the ultrasonic transducer is incorporated, and the control apparatus which controls it has been exemplarily described. The embodiment is not restricted to this, and may be applied also to an endoscope apparatus comprising an endoscope which does not incorporate an ultrasonic transducer, and a control apparatus.

The endoscope apparatus of the invention comprises: the connector cover which is attached to be slidable between the close position where the control-apparatus connector is covered, and the open position where the control-apparatus connector is exposed, the open position being located below the close position, the press projection being formed integrally with the connector covers the press projection being substantially perpendicular to the slide direction, projecting toward the outside of the case, and formed in accordance with the endoscope connector; and the urging member which urges the connector cover from the open position to the close position. When the endoscope connector is placed on the press projection to press down the press projection, the connector cover is moved from the close position to the open position against the urging force of the urging member, thereby enabling the endoscope connector to be connected with the control-apparatus connector through the opening. Therefore, the connecting operation can be easily performed, and excellent waterproof and dustproof properties can be held.

The entire disclosure of each and every foreign patent application from which the benefit of foreign priority has been claimed in the present application is incorporated herein by reference, as if fully set forth.

What is claimed is:

1. An endoscope apparatus comprising:
   an endoscope including an endoscope connector in one end portion; and
   a control apparatus that controls the endoscope, the control apparatus including:
   a case having an opening;
   a control-apparatus connector in an inner part of the opening, the control-apparatus connector adapted to be connected with the endoscope connector;

a connector cover attached to be slidable between a closed position where the control-apparatus connector is covered and an opened position where the control-apparatus connector is exposed, the opened position being located below the closed position, wherein the connector cover includes a press projection that is formed integrally with the connector cover, that is substantially perpendicular to a slide direction, projecting toward an outside of the case, and that is formed in accordance with the endoscope connector; and an urging member that urges the connector cover from the opened position to the closed position, wherein, when the endoscope connector is placed on the press projection and pressed down, the connector cover is moved from the closed position to the opened position against an urging force of the urging member, so as to enable the endoscope connector to be connected with the control-apparatus connector through the opening, a surface of the press projection, which faces the endoscope connector when the endoscope connector is connected with the control-apparatus connector, is concave, wherein the case integrally comprises, above the opening, a guide piece that extends upwardly from the opening and guides the endoscope connector toward the press projection, and a peak portion that is disposed on the case and above the opening and the guide piece, and projects in a direction that is perpendicular to the slide direction.

2. An endoscope apparatus according to claim 1,
wherein the press projection includes, in both side end portions thereof, guide projections extending along a projection direction in which the press projection projects, and surfaces of the guide projections which are opposed to each other are tapered.

3. An endoscope apparatus according to claim 1,
wherein each of the case and the endoscope connector comprises a positioning mark, and the endoscope connector is aligned to a predetermined direction with respect to the control-apparatus connector by matching positions of the positioning marks with each other.

4. An endoscope apparatus according to claim 1,
wherein the control apparatus further comprises a damper member that resists the urging force of the urging member to reduce a speed of the connector cover that returns from the opened position to the closed position.

5. An endoscope apparatus according to claim 1, wherein the concaved surface of the press projection is lowered from a proximal end of the press projection to a distal end of the press projection.

6. An endoscope apparatus according to claim 1, further comprising:

a lock member including an engaged projection which projects from a cylindrical outer peripheral face thereof, wherein the lock member is in the endoscope connector, and the engaged projection is configured to be engaged with an engagement groove of the control-apparatus connector, the lock member passes through an interior of the connector to project toward an insertion side, a grip member is formed integrally with an insertion-side tip end portion of the lock member, and when the grip member is rotated, the lock member is integrally rotated with the grip member.

7. An endoscope apparatus according to claim 1, wherein the guide piece projected in a direction that is perpendicular to the slide direction.

8. An endoscope apparatus according to claim 7, wherein when the connector cover is located at the closed position, an end of a guide projection and an end of the guide piece are substantially adjacent to each other.

* * * * *